United States Patent
Gan et al.

(10) Patent No.: US 8,920,835 B2
(45) Date of Patent: Dec. 30, 2014

(54) PALIPERIDONE DOUBLE-LAYERED OSMOTIC PUMP CONTROLLED RELEASE TABLET AND PREPARATION METHOD THEREOF

(75) Inventors: Yong Gan, Shanghai (CN); Chunliu Zhu, Shanghai (CN); Qingmin Yang, Jinan (CN); Jingyi Wang, Jinan (CN); Xiaoqing Zheng, Jinan (CN); Li Gan, Shanghai (CN); Xinxin Zhang, Shanghai (CN)

(73) Assignees: Shanghai Institute of Materia Medica, Chinese Academy of Sciences, Shanghai (CN); QILU Pharamceutical Co., Ltd., Shandong (CN)

( * ) Notice: Subject to any disclaimer, the term of this patent is extended or adjusted under 35 U.S.C. 154(b) by 261 days.

(21) Appl. No.: 13/512,402

(22) PCT Filed: Nov. 22, 2010

(86) PCT No.: PCT/CN2010/078967
§ 371 (c)(1),
(2), (4) Date: Aug. 8, 2012

(87) PCT Pub. No.: WO2011/063732
PCT Pub. Date: Jun. 3, 2011

(65) Prior Publication Data
US 2012/0301547 A1    Nov. 29, 2012

(30) Foreign Application Priority Data
Nov. 26, 2009   (CN) .......................... 2009 1 0199425

(51) Int. Cl.
*A61K 9/24*   (2006.01)
*A61K 9/28*   (2006.01)
*A61K 31/519*  (2006.01)
*A61P 25/18*  (2006.01)
*B05D 5/00*   (2006.01)
*A61K 9/00*   (2006.01)
*A61K 9/20*   (2006.01)
*A61K 31/517* (2006.01)

(52) U.S. Cl.
CPC ............. *A61K 9/0004* (2013.01); *A61K 9/2086* (2013.01); *A61K 9/2866* (2013.01); *A61K 31/517* (2013.01)
USPC ...... 424/465; 424/468; 424/473; 514/259.41; 427/2.21

(58) Field of Classification Search
None
See application file for complete search history.

(56) References Cited

U.S. PATENT DOCUMENTS

| 6,245,357 | B1 * | 6/2001 | Edgren et al. .................. 424/473 |
| 2007/0026067 | A1 * | 2/2007 | Yam et al. ..................... 424/468 |
| 2007/0190137 | A1 | 8/2007 | Iran et al. |

FOREIGN PATENT DOCUMENTS

CN            162840           6/2005

OTHER PUBLICATIONS

International Search Report for PCT/CN2010/078967, mailed Mar. 10, 2011.

* cited by examiner

*Primary Examiner* — Frederick Krass
*Assistant Examiner* — Michael P Cohen
(74) *Attorney, Agent, or Firm* — Nixon & Vanderhye P.C.

(57) ABSTRACT

A paliperidone double-layered osmotic pump controlled release tablet and the preparation method thereof are disclosed. The double-layered osmotic pump controlled release tablet comprises a rigid membrane, a push layer, a drug layer, an isolation layer and an aesthetic coating, wherein the rigid membrane contains a semi-permeable polymer, a porogen and/or a plasticizer and has one or more drug release orifices on one end, the push layer comprises an expanding material, an osmotic agent, a binder, a colorant and a lubricant, the drug layer contains a pharmaceutically active ingredient, a hydrophilic polymer, an osmotic agent, a colorant, a lubricant and an antistatic agent, the isolation layer is located between the inner surface of the rigid membrane and the push layer, and contains a hydrophilic polymer. The paliperidone double-layered osmotic pump controlled release tablet shows an increasing drug release rate at early stage and keeps a constant drug release rate at later stage.

22 Claims, 7 Drawing Sheets

Release curves of the paliperidone controlled release tablet in different media

Release curves of the paliperidone controlled release tablet in gastrointestinal fluid Release curve of paliperidone Average release rate of the paliperidone double-layered osmotic pump controlled release tablet Average release rate of the commercially available capsule-shaped paliperidone osmotic pump controlled release tablet

PALIPERIDONE DOUBLE-LAYERED OSMOTIC PUMP CONTROLLED RELEASE TABLET AND PREPARATION METHOD THEREOF

This application is the U.S. national phase of International Application No. PCT/CN2010/078967 filed 22 Nov. 2010 which designated the U.S. and claims priority to CN Patent Application No. 200910199425.9 filed 26 Nov. 2009, the entire contents of each of which are hereby incorporated by reference.

FIELD OF THE INVENTION

The present invention relates to a controlled release dosage form of a benzoisoxazole derivative, and more particularly, to a paliperidone double-layered osmotic pump controlled release tablet and preparation method thereof. The paliperidone double-layered osmotic pump controlled release tablet may be used for the treatment of schizophrenia and bipolar mania.

BACKGROUND OF THE INVENTION

Schizophrenia, which is characterized by the change of basic personality, the schism of thinking, feeling and behavior, and the disharmony of psychomotility and surroundings, is a most common type of mental illness and belongs to the severe type. Schizophrenia mainly occurs in young and middle-aged people without organic change, and it is a functional psychosis. Patients suffering from schizophrenia generally have no impediment in consciousness and intelligence, but when there is schizophrenic attack, it not only affects the labor capacity of the patients, but also exerts great influence on working, studying, living and socializing of the patients themselves. Medication therapy is one of the most commonly-used and effective treatment methods so far, and it can not only effectively control the schizophrenic symptoms, but also significantly control and reduce the frequency and intensity of the onset of the disease.

Antipsychotics are usually classified into two categories of typical and atypical according to the mechanism of action: (1) typical antipsychotics (traditional antipsychotics), whose representatives include chloropromazine, haloperidol and the like; (2) atypical antipsychotics (nontraditional antipsychotics), whose representatives include paliperidone, clozapine, risperidone and the like. Compared with the traditional medicines, the atypical antipsychotics have lower affinity with dopaminergic D2 receptor, but have higher affinity with 5-hydroxytryptamine and noradrenergic receptor. Meanwhile, atypical antipsychotics have broad treatment spectrum and significant effect on negative symptoms when compared to traditional medicines, and they have high security, fewer adverse effect and low dosage, significantly improving the compliance of the patients.

Paliperidone (9-hydroxyrisperidone), which is a benzoisoxazole derivative, is a new type of antipsychotic, and the exact mechanism of action thereof is still unclear. It is now thought that paliperidone blocks the signal transmission of neurotransmitters in brain of the patients by blocking dopaminergic (D), 5-hydroxytryptamine-2A (5HT2) and adrenergic receptors. Paliperidone has an oral bioavailability of 28%, a plasma protein binding rate of 74%, a half-life of the terminal elimination phase of about 23 h, and an apparent volume of distribution of 487 L. The major adverse effects after oral administration of paliperidone include anxiety, somnolence, dizziness, constipation, extrapyramidal symptoms and the like.

U.S. Pat. Nos. 5,158,952; 4,804,663; 4,352,811 and 4,458,076 describe in detail the paliperidone compound and preparation process thereof.

Chinese patent publication No. CN101,264,084 provides a method for the treatment of psychiatric patients having or at risk of hepatic impairment, which comprises administering a therapeutically effective dose of paliperidone, its pharmaceutically acceptable acid addition salts, enantiomer and esters thereof to psychiatric patients in need thereof.

In the international application Nos. WO 00/35419, WO 96/31201, WO 01/34120 and U.S. Pat. Nos. 5,654,008; 5,650,173; 5,770,231; 6,077,843; 6,368,632; 6,110,923; 5,695,168; 5,692,477; 5,871,778; 5,656,299, paliperidone is used as the model drug to prepare various dosage forms such as liquid gelatin capsule, transdermal patch, long-acting injection implant and the like, but the preparation of osmotic pump controlled release tablet using paliperidone is not disclosed.

Osmotic pump controlled release tablet is an oral controlled release drug delivery system based on osmosis, which is a general technology for the preparation of sustained/controlled release dosage form. U.S. Pat. Nos. 3,845,770; 3,916,899; 3,995,631; 4,008,719; 4,160,020; 4,034,758; 4,327,725; 4,578,075; 4,681,583; 4,783,337; 5019397; 5,156,850 describe the osmotic pump controlled release technology in detail, which are incorporated herein by reference. Osmotic pump controlled release dosage form usually has the following advantages: (1) it possesses a preset drug-release kinetic behavior; (2) it is less influenced by the factors such as pH of the medium, gastrointestinal peristalsis and food; and has a good relevance between in vivo and in vitro; (3) it is capable of avoiding the phenomenon of large fluctuation range of blood concentration caused by common oral dosage forms; (4) it is capable of reducing the frequency of administration, and improving the compliance of patients.

On the basis of above advantages of the osmotic pump controlled release tablet, paliperidone may be combined with the osmotic pump controlled release drug delivery system to prepare paliperidone osmotic pump controlled release tablet, as a preferred oral osmotic (OROS) dosage form, so as to further reduce the neural adverse reactions (mainly extrapyramidal symptoms) of atypical antipsychotics, to decrease the fluctuation of blood concentration, to increase therapeutic effect, and to improve the compliance of patients.

At present, a commercially available paliperidone sustained release tablet (trade name: Invega) is a benzoisoxazole antipsychotic developed by Janssen L P, a member of Johnson & Johnson, US, and it was approved by FDA for marketing on Nov. 29, 2005, which was indicated for the treatment of schizophrenia and bipolar mania.

Chinese patent publication No. CN1,684,670A discloses a dosage form of substantially releasing paliperidone and preparation method thereof. The sustained release dosage form provides a therapeutically effective plasma concentration of paliperidone when administered once daily. The capsule-shaped sustained release tablet containing paliperidone of the invention is orally administered to release paliperidone at a substantially ascending release rate during the prolonged period of time. This invention describes in detail the preparation method of paliperidone capsule-shaped osmotic pump controlled release tablet, the main excipient of the tablet core is a polymeric material—polyoxyethylene. Unfortunately, however, we have found that the three-layered capsule shaped osmotic pump controlled release tablet still has some disadvantages for the following reasons, for example:

(1) It needs a special preparation process with a high production cost. The preparation process of the three-layered osmotic pump controlled release tablet is comparatively complicated, wherein it requires to prepare two kinds of drug layer particles with different drug contents and determined respectively the drug content, and then press into tablet, and thus the preparing period is long with more workload. The common used doses of paliperidone include 3 mg, 6 mg, and 9 mg, which belong to the low dose drug, and thus paliperidone has high requirements for content uniformity of the tablet core. But for a three-layered tablet, it is more difficult to achieve a satisfactory content uniformity Therefore, the preparation of a three-layer capsule shaped osmotic pump controlled release tablet requires a specific tablet compressor (three-layered tablet press), with a higher machining precision.

(2) The main excipient for tablet core has a poor thermal stability. Polyoxyethylene is a kind of high molecular polymer with poor thermal stability and which has low glass transition temperature (62~67° C.). Due to the above features, it has the following problems during the industrial production and storage. (i) It is difficult to dry off the solvent during granulation process. The drying temperature for polyoxyethylene is generally less than 40° C., thus easily leading to problems of insufficient dryness and high residue of organic solvent; and if a complete dryness is required, it requires a relatively long drying duration, which results in higher production cost. (ii) The storage temperature of the tablet should not be too high, and the tablet has to be stored in a cool, dark place, which increases the storage cost. Meanwhile, a high storage temperature tends to cause some changes in the physicochemical properties of polyoxyethylene, such as, the oxidative degradation of polyoxyethylene, the decrease in the viscosity of the tablet core, which eventually result in the acceleration of the release of the controlled release tablet, and this will increase potentially dangerous factors to the treatment of patients. (iii) During high-speed tablet pressing, the punch die repeatedly rubs to generate heat, and when the temperature reaches about 50° C., phenomena such as sticking, rough appearance of tablet core, rolled edge in part of the tablet core would likely appear. Therefore, it usually requires a special cooling equipment to control the temperature of punch die. For the osmotic pump controlled release tablet, the rolled edge in part of the tablet core is likely to cause vulnerable point in the coating membrane in the said part, which may lead to the fracture of the coating membrane in the course of release. Consequently, it affects the release rate of the drug, and more seriously, a sudden release of the drug caused by the fracture of the coating membrane may directly contribute to the fluctuation of blood concentration, thus increase the potential risk and adverse reaction of the administration of the psychotic patients, which goes against the purpose for preparing osmotic pump controlled release tablet.

(3) The three-layered capsule shaped osmotic pump controlled release system releases paliperidone at a substantially ascending release rate, which results in a relatively large fluctuation range of blood concentration, and thus reduces the safety, effectiveness and compliance of the administration.

Therefore, there is a need to provide a paliperidone osmotic pump controlled release tablet, which has a simple preparation process, low cost excipients for tablet core and good thermal stability, and is capable of effectively control the release rate of the drug to keep the curve of blood concentration smooth and reduce its fluctuation, and thus improve safety, effectiveness and compliance of the administration.

DETAILED DESCRIPTION OF THE INVENTION

Technical Problems

To solve the above problems, one object of the present invention is to provide an double layered osmotic pump controlled release tablet comprising a benzoisoxazole derivative, specifically, a paliperidone double layered osmotic pump controlled release tablet, which shows an increasing release rate in early stage and maintaining a constant release rate in the later stage. The paliperidone double layered osmotic pump controlled release tablet has advantages of simple preparation process, low cost excipients for the tablet core, and good thermal stability etc., and has an improved drug release curve, a release rate free of the influence of gastrointestinal peristalsis and pH value, a small individual difference, a stable plasma concentration, and a long-term therapeutic effectiveness, eliminating the peak-trough phenomenon and reducing adverse reactions, and thereby increasing the safety, efficacy and compliance of the administration. The paliperidone double layered osmotic pump release tablet according to the present invention can be used for the treatment of schizophrenia and bipolar mania.

Another object of the present invention is to provide a method for preparation of the above paliperidone double layered osmotic pump release tablet.

Technical Solutions

To achieve the above objects, the present invention Provides a paliperidone double layered osmotic pump release tablet showing an increasing release rate in early stage and maintaining a constant release rate in later stage, which comprises:

a moisture-permeable rigid membrane shell having one or more drug-release orifices at one end thereof, which is made of a controlled release layer composition comprising a semipermeable polymer, as well as a porogen and/or a plasticizer;

a push layer inside the rigid membrane shell and away from the side of the release orifices, which is made of a push layer composition comprising a expansion material, an osmotic agent, a binder, and optionally, a colorant and a lubricant;

a drug layer inside the rigid membrane shell, adjacent to the release orifices and directly contacting with the push layer, which is made of a drug layer composition comprising a pharmaceutically active ingredient, one or more kinds of hydrophilic polymer carriers, and optionally, a osmotic agent, a colorant, a lubricant and an antistatic agent, based on total weight of the drug layer composition;

an isolation layer located between the inside surface of the rigid membrane shell and a tablet core consisting of the drug layer and the push layer, which is made of an isolation layer composition comprising one or more hydrophilic polymers and optionally, a pharmaceutically active ingredient, based on the total weight of the isolation layer composition;

an optional aesthetic coating layer coating on the outer surface of the rigid membrane shell, which is made of an aesthetic coating layer composition comprising coating powder for forming the aesthetic coating, and optionally, one or more excipients selected from the group consisting of a colorant, a plasticizer, a opacifying agent, an anti-sticking agent and the like;

wherein the hydrophilic polymer carrier in the drug layer is selected from the group consisting of povidone, copolymerized povidone, carbomer, hydroxypropyl cellulose, hypromellose and mixtures thereof.

The present invention use a mature process technique with high machining precision to prepare the paliperidone double layered osmotic pump release tablet, which will facilitate the manufacturers to greatly simplify the production process and reduce production costs. At the same time, in order to solve the problem of the thermal stability of the excipients in the tablet core of the three-layered osmotic pump release tablet described in Chinese patent application No. CN 1,684,670 A, the inventors screened and designed a novel drug layer composition and a novel push layer composition, and prepared the paliperidone double layered osmotic pump release tablet in company with an isolation layer composition. The new designed tablet core has a good thermal stability with a high glass transition temperature, therefore solving the drying problems, sticking problems in the high-speed tablet-pressing and the storage problems of the excipients and tablet. Additionally, the new designed formulation is well compressible and suitable for high-speed tablet-pressing, and the preparation process thereof is mature, stable and reproducible. On the other hand, the excipients used in the novel formulation is non-toxic, has no irritation for skin, no allergic reactions, and will not be absorbed by gastrointestinal tract, and mucosa after oral administration. Therefore, the effect of the factors such as gastrointestinal peristalsis, pH, food and the like on the drug release can be avoided. At the same time, the specific designed double layered osmotic pump release tablet can show a increasing release rate at the initial stage, and it will release the drug at a constant release rate after plasma concentration reaching an effective concentration. This release behavior can not only ensure that the plasma concentration able to rapidly achieve the therapeutically effective concentration in the early stage, but also guarantee a more stable plasma concentration curve in the later stage of the drug release and reduce the fluctuation of plasma concentration, thereby greatly improves the safety, efficacy and compliance of the administration.

The paliperidone double layered osmotic pump controlled release tablet according to the present invention can provide at least 3 hours, preferably 5 hours of an early stage with the increasing drug-release rate, and at least 5 hours, preferably 6 to 12 hours of a later stage at a constant drug-release rate. The designed drug-release behavior can ensure a rapid release at the early stage to reach the therapeutic concentration in order to achieve a rapid onset, and also guarantee a relative constant plasma concentration by the constant release rate in the later stage.

The term of "increasing release rate" in the present invention means that the release rate of the active substance from the membrane shell in a certain period increases with the time measured by a release determination method. The term of "constant release rate" in the present invention means that release rate of the active substance from the membrane shell is basically constant in a certain period measured by a release determination method, and the relative standard deviation thereof does not exceed 25%.

In the paliperidone double layered osmotic pump controlled release tablet according to the present invention, based on the total weight of the controlled release tablet, the weight percentages of various layers are as follows: the drug layer takes up 10 to 80 wt %, preferably 20 to 70 wt %, more preferably 30 to 70 wt %, and most preferably 30 to 60 wt %; the push layer takes up 15 to 60 wt %, preferably 20 to 55 wt %, more preferably 20 to 50 wt %, and most preferably 25 to 50 wt %; the isolation layer takes up 0.1 to 30 wt %, preferably 2 to 30 wt %, more preferably 5 to 25 wt %, and most preferably 10 to 25 wt %; the membrane shell takes up 0.1 to 15 wt %, preferably 0.5 to 12 wt %, more preferably 2 to 10 wt %, and most preferably 4 to 10 wt %; the aesthetic coating layer takes up 0 to 20 wt %, preferably 0.1 to 15 wt %, more preferably 1 to 10 wt %, and most preferably 2 to 8 wt %.

The drug layer according to the present invention is made of a drug layer composition comprising a pharmaceutically active ingredient, one or more kinds of hydrophilic polymer carriers and, optionally, excipients such as an antistatic agent, an osmotic agent, a lubricant, a colorant, etc.

The pharmaceutically active ingredient is selected from the group consisting of paliperidone, the pharmaceutically acceptable salts or esters thereof. Based on the total weight of the drug layer composition, the active ingredient takes up 0.1 to 25 wt %, preferably 1 to 20 wt %, more preferably 2 to 15 wt % in the drug layer composition.

The hydrophilic polymer carrier can provide a uniform and controlled release rate of the pharmaceutically active ingredient for the paliperidone double layered osmotic pump controlled release tablet according to the present invention, and is selected from the group consisting of povidone, copolymerized povidone, carbomer, hydroxypropyl cellulose, hypromellose and mixtures thereof. These hydrophilic polymer carriers have relatively low price, are physiological inert materials with a high oral safety, and are also thermal stable and have high glass transition temperature so as to solve the problem of thermal stability of the excipients in tablet core. The proportion of the hydrophilic polymer carrier in the drug layer composition is 65 to 99%, preferably 70 to 95% based on the total weight of the drug layer composition.

The inventors, during the preparation, unexpectedly found that there is a strong electrostatic effect between the active ingredient paliperidone and excipients in the mixing process so that the active ingredient is easily adhered to the inner wall of the container, resulting in poor content uniformity of the materials. In order to prevent the unqualified content uniformity due to the uneven mixing of the materials, an antistatic agent is added into the formulation of the drug layer. The antistatic agent includes one or more selected from the group consisting of silicon dioxide, stearic acid, and polyethylene glycol, preferably is silicon dioxide. Based on the total weight of the drug layer, the antistatic agent takes up 0 to 8 wt %, preferably 0.1 to 5 wt %, more preferably 0.1 to 2 wt % in the drug layer.

The present invention is an oral controlled-release drug delivery system based on permeation. The use of an osmotic agent can facilitate the hydration rate of the tablet core of drug layer. The osmotic agent is selected from the group consisting of sodium chloride, lactose, mannitol, sorbitol, glucose, sucrose, fructose and mixture thereof, preferably is sodium chloride, or lactose. The osmotic agent takes up 0 to 30 wt % in the drug layer composition based on the total weight of the drug layer composition.

Since the content of the pharmaceutically active ingredient is low in the paliperidone double layered osmotic pump controlled release tablet according to the present invention, the addition of a lubricant can improve the granules' flowability for the drug layer and push layer during the high-speed tablet-pressing and ultimately improve the labeled amount and content uniformity of the final product. The used lubricant should be inert to the pharmaceutically active ingredients of the present dosage form, and it is selected from the group consisting of the following known materials for the skilled person in the art, such as stearic acid, magnesium stearate, sodium stearylfumarate, talc, waxes, and their mixtures. The lubricant takes up 0 to 3%, preferably 0.5 to 2% in the drug layer, based on the total weight of the drug layer composition.

The use of a colorant can facilitate to identify the drug layer and the push layer. However, the color of the drug layer and the push layer is inconsequential, and color selection does not influence the usage and effect of the present invention. The colorants can be one or more selected from the group consisting of iron oxide red, iron oxide yellow, iron oxide purple, iron oxide black and mixture thereof. The colorant takes up 0 to 2%, preferably 0.1 to 1%, in the drug layer composition, based on the total weight of the drug layer composition.

The push layer is a high molecular material layer with self-expandable and promoting effects. It is adjacent to the drug layer, and made of a push layer composition. The push layer composition usually comprises pharmaceutical excipients such as an expansion material, an osmotic agent, a binder, and optionally, a colorant and a lubricant etc.

The expansion material is generally a high molecular polymer, which will swell after absorbing water in an aqueous media so as to push the release of drug from the drug layer composition. The expansion material is selected from the group consisting of the following known materials for a skilled person in the art, such as sodium carboxymethyl starch, low substituted hypromellose, hypromellose, hydroxypropyl cellulose, croscarmellose sodium, crospovidone, carbomer and mixture thereof, and preferably a mixture of sodium carboxymethyl starch, carbomer and hypromellose. The expansion material takes up 20 to 80%, preferably 30 to 75%, more preferably 30 to 60% in the push layer composition, based on the total weight of the push layer composition.

The effect and selectable categories of the osmotic agent used in the push layer composition are same as that used in the drug layer composition. The osmotic agent in the push layer composition takes up 10 to 45%, preferably 20 to 35% based on the total weight of the push layer composition.

The binder is generally selected from the group consisting of povidone, copolymerized povidone, hypromellose and mixture thereof. The binder in the push layer composition takes up 0 to 30%, preferably 10 to 30% based on the total weight of the push layer composition.

The effect and selectable categories of the lubricant used in the push layer composition are same as that used in the drug layer composition. The lubricant in the push layer composition takes up 0 to 3%, preferably 0.1 to 1.5% based on the total weight of the push layer composition.

The effect and selectable categories of the colorant used in the push layer composition are same as that used in the drug layer composition. The colorant in the push layer composition takes up 0 to 2%, preferably 0.1 to 1% based on the total weight of the push layer composition.

The above drug layer and push layer constitute the tablet core of the paliperidone double layered osmotic pump release tablet according to the present invention. The method for preparing the double layered tablet is the common option for the skilled person in the art, for example, a single punch tablet press or double-layer tablet press can be applied to produce the tablet core of the paliperidone double layered osmotic pump release tablet according to the present invention.

The isolation layer is used to provide protection for the tablet core of the paliperidone double layered osmotic pump release tablet according to the present invention. It is a novel combination to combine the main excipients of the tablet core and the pharmaceutically active ingredient of the present dosage form in company with the isolation layer. The paliperidone double layered osmotic pump release tablet prepared by this combination is characterized by significantly controlled release, so that the safety of the drug can be further improved.

The isolation layer may be formed through dissolving the isolation layer composition in a proper solvent to prepare an isolation layer coating solution, and then spray-coated on the tablet core and drying, or may be made by tablet press. Preferably, the isolation layer is made by the tablet coating. The isolation layer composition consists of a hydrophilic material, which is selected from the group consisting of the following known materials for a person skilled in the art, such as hypromellose, povidone, copolymerized povidone, hydroxyethyl cellulose, polyoxyethylene, polyethylene glycol and mixtures thereof, preferably hypromellose, povidone, copolymerized povidone, polyethylene glycol and mixtures thereof. The proper solvent is selected from the group consisting of ethanol, water, acetone, isopropyl alcohol or a mixture thereof.

The thickness of the isolation layer can impact the release curve of the pharmaceutical dosage form, and it may be controlled by coating duration and amount. Based on the total weight of the double layered tablet core, the weight gain of the isolation layer usually is no more than 40 wt % of the tablet core. The thickness of the isolation layer coating is usually between 0.05 and 3 mm.

In some embodiments, the isolation layer composition may further comprise the pharmaceutically active ingredient, paliperidone. Based on the total weight of the isolation layer composition, the pharmaceutically active ingredient takes up 0 to 30 wt %, preferably 0 to 15 wt % in the isolation layer. The release behavior, especially the—drug-release behavior in the early release stage of the present dosage form, may be adjusted by adjusting the content of the pharmaceutically active ingredient in the isolation layer, which has been extensively investigated through specific examples (FIG. 9 to FIG. 11).

The rigid membrane shell is the key point of the double layered osmotic pump controlled release system, and it is the controlled release layer in the present invention. The presence of a rigid membrane shell may allow the penetration of outer liquids, such as water and biological fluid, and prevent the penetration of the pharmaceutically active ingredient, the osmotic agent and the permeable polymer. In the present invention, after water penetrates the rigid membrane shell into the tablet core such that the push layer is hydrated and swollen to promote the hydrated drug layer suspension releasing from the release orifices on the rigid membrane shell. The method for preparing the rigid membrane shell is a common option for the skilled person in the art, and as an example, it can be prepared by dissolving the controlled release layer composition in a proper solvent to prepare a controlled release layer coating solution and then spray the controlled release layer coating solution on the tablet core using a high efficient coating pan and then drying. The controlled release layer composition comprises a semi-permeable controlled release membrane material, a plasticizer and a porogen.

The semi-permeable controlled release membrane material is known for the skilled person in the art, and is selected from the group consisting of cellulose acetate, ethyl cellulose, acrylic resin and mixtures thereof.

For adjusting the permeability of water through the rigid membrane shell, a plasticizer and a porogen may be added. The porogen can improve the permeability of water through the rigid membrane shell. Based on the total weight of the controlled release layer composition, the amount of the porogen is usually 0 to 50%, preferably 0 to 30%. The porogen may include glycerin, povidone, copolymerized povidone, propylene glycol, polyethylene glycol, water-soluble inorganic salts and mixtures thereof.

The plasticizer enables the membrane shell with more flexibility and extensibility, and the use of the plasticizer can affect the release rate of the drug. Based on the total weight of the controlled release layer composition, the amount of the plasticizer is usually about 0 to 20%, preferably 0 to 15%. The plasticizer may be selected from the group consisting of dimethyl phthalate, diethyl phthalate, dibutyl sebacate, triethyl citrate, tributyl citrate, tributyl acetylcitrate, glycerol acetate, castor oil and mixtures thereof.

The proper solvent for preparing the controlled release layer coating solution according to the present invention is selected from the group consisting of acetone, water, ethanol, isopropyl alcohol, methylene chloride, methanol, ethyl acetate and mixtures thereof.

Additionally, an aesthetic coating layer may be coated on the outside of the rigid membrane shell of the paliperidone double layered osmotic pump controlled release tablet according to the present invention, to provide additional functions, such as aesthetic appearance, moisture-protecting, light-protecting etc., but have no influence on the drug release of the paliperidone double layered osmotic pump controlled release tablet according to the present invention. Based on the total weight of the paliperidone double layered osmotic pump controlled release tablet, the proportion of aesthetic coating layer is about 0 to 20%, preferably 0.1 to 15%.

The aesthetic coating layer is made of an aesthetic coating layer composition. The aesthetic coating layer composition comprises a coating powder for forming the aesthetic coating, and, optionally, one or more excipients selected from the group consisting of a colorant, a plasticizer, an opacifying agent, an anti-sticking agent etc., and the using amounts thereof are common selections for a skilled person in the art. The coating powder for the aesthetic coating is the common option for a skilled person in the art, and is selected from the group consisting of commercially available Opadry and other coating powders capable of forming the aesthetic coating. The opacifying agent may include titanium dioxide, talc, silicon dioxide, and mixtures thereof. The anti-sticking agent is mainly selected from the group consisting of talc, magnesium stearate, glycerol monostearate and mixtures thereof.

In another aspect, the invention provides a method for preparing the paliperidone double layered osmotic pump controlled release tablet, comprising the steps of:

(1). preparing a drug layer composition;
(2). preparing a push layer composition;
(3). pressing a double-layered tablet core;
(4). coating an isolation layer on the obtained the double-layered tablet core;
(5). coating a controlled release layer on the double-layered tablet core;
(6). perforating drug release orifices on the coated tablet; and
(7). optionally, coating an aesthetic coating layer.

The preparation method for the granules of the drug layer composition is a common selection for a skilled person in the art, and for example, it may be performed by dry granulation or wet granulation. Since the one step granulation in a fluid bed is simple, quick and high effective, it is preferably here to granulate by a wet granulation process through a fluid bed. The materials for drug layer composition in formulated amount are added into a fluid bed and uniformly mixed, sprayed with 95% ethanol solution to prepare the drug layer composition granules of the paliperidone double layered osmotic pump controlled release tablet according to the present invention, dried completely and added with a lubricant to be ready for use.

The preparation method for the push layer composition in the present invention is similar to that for the drug layer composition, and preferably, but not limited to, the fluid bed process. The materials for the push layer composition in formulated amount are added into a fluid bed and uniformly mixed, sprayed with a solvent to prepare granules of the push layer composition of the paliperidone double layered osmotic pump controlled release tablet according to the present invention, dried completely and added with a lubricant to be ready for use.

The pressing method for the double-layered tablet core is a conventional option for a skilled person in the art, and for example, may be performed by a single punch tablet press or a double-layered tablet press to produce the double-layered tablet core of the paliperidone double layered osmotic pump controlled release tablet according to the present invention. A proper amount of granules of the drug layer composition is first added into a tablet slot to perform a pre-press, and then the granules of the push layer composition are added to press into a double-layered tablet core with appropriate hardness.

The method for coating an isolation layer and/or a controlled release layer on the double-layered tablet core is a common option for a skilled person in the art, and for example, it may be performed by coating the prepared double-layered tablet core using a high efficient coating pan. The coating solution of the isolation layer composition in formulated amount is spray-coated on the tablet core to a predetermined weight increment, and dried to remove the solvent to form an isolation layer. After that, the controlled release coating is done.

The paliperidone double layered osmotic pump controlled release tablet according to the present invention comprising at least one drug release orifice. The drug release orifice can be prepared by mechanical drilling or laser drilling. The geometry of the release orifice is not limited, and may be any geometric shape, such as round, oval, square, triangle etc., and the pore size is in a range of 0.3 to 1.2 mm.

FIG. 1 is a structure diagram of the paliperidone double layered osmotic pump controlled release tablet according to an embodiment of the present invention. As shown in FIG. 1, the rigid membrane shell 2 contains at least one drug release orifice 1; the push layer 5 is located inside the rigid membrane shell and at the side away from the release orifice 1; the drug layer is located inside the rigid membrane shell, and at the side adjacent to the release orifice 1 and directly contacting with the push layer 5; the isolation layer 3 is sandwiched between the inside surface of the rigid membrane shell and the tablet core consisting of the drug layer 4 and the push layer 5.

The step of coating an aesthetic coating layer is optional. In case of no aesthetic layer in the paliperidone double layered osmotic pump controlled release tablet according to the present invention, this step is unnecessary. The coating method for the aesthetic layer is a common option for a skilled person in the art. As an example, the materials for the aesthetic layer composition may be dissolved in a proper solvent to prepare an aesthetic layer coating solution, which is then coated on the paliperidone double layered osmotic pump controlled release tablet according to the present invention and dried to form the aesthetic layer.

The paliperidone double layered osmotic pump controlled release tablet according to the present invention is a controlled release preparation prepared by the osmotic pump preparation technique, and it can release the drug under a predetermined release rate. After administration, the drug release system will be activated through absorbing moisture in the gastrointestinal tract, and the expansion materials (high molecular compounds) of the push layer as the driving part for drug release will absorb moisture to swell to push the hydrated drug layer suspension out of the release orifice under a predetermined release rate. The release rate is not impacted by gastrointestinal peristalsis and pH value, the individual difference is small, the plasma concentration is stable, and the therapeutic effectiveness is long, thus eliminating the peak-trough phenomenon and fewer adverse reactions.

Beneficial Effects of the Invention

The beneficial effects of the present dosage form are based on the advantages of the osmotic pump controlled release dosage form, specifically embodied as followings.

(1) The dosage form according to the present invention has a unique release behavior, that is, it shows an increasing drug release rate at early release stage, and a constant release rate at the later release stage. The designed drug release behavior can ensure the quick release of the drug at early stage so as to achieve a rapid onset of the drug, and at the same time, the later steady release rate can avoid the adverse reaction (extrapyramidal symptoms) resulted from the fluctuation of plasma concentration. The results of the in vivo pharmacokinetic investigation show that the paliperidone double layered osmotic pump controlled release tablet according to the present invention can quickly onset, and maintain a relatively constant plasma concentration of the active substance and a sustained therapeutic effectiveness of the active substances, and therefore, the fluctuation in plasma concentration is smaller and compliance is better.

(2) The impact of the factors such as the pH of the media, gastric peristalsis and food is small, and the in vitro and in vivo relevance is good.

(3) The phenomena of large fluctuation range in the plasma drug concentration caused by common oral dosage form is avoided.

(4) The frequency of administration is reduced, and the safety, efficacy and compliance of the administration are greatly improved.

(5) The present invention uses a double-layered osmotic pump controlled release system. Compared with the commercially available capsule-shaped controlled release tablets, the present invention greatly simplifies the production process, and adopts the common production equipments without any special equipment, and thus decreases production cost greatly and is suitable for industrial production.

(6) The formulation of the tablet core has good thermal stability and high glass transition temperature, and thus solving the problems in drying process, sticking in the process of high-speed tablet-pressing and the problems in the storage of the excipients and tablet, which are resulted from using polyoxyethylene as an excipient for the tablet core. The present invention provides a formulation which has a good compressibility, smooth tablet surface and is suitable for high-speed tablet-pressing, and adopts a mature and stable preparation technology, and thus has a broader prospect for industrial production.

In the present invention, the terms of "rigid membrane shell", "controlled release layer", "controlled release coating membrane" and "controlled release coating" etc. present in different positions for convenient description. The person skilled in the art should understand that these different expressions have the same meaning.

Figure 1:
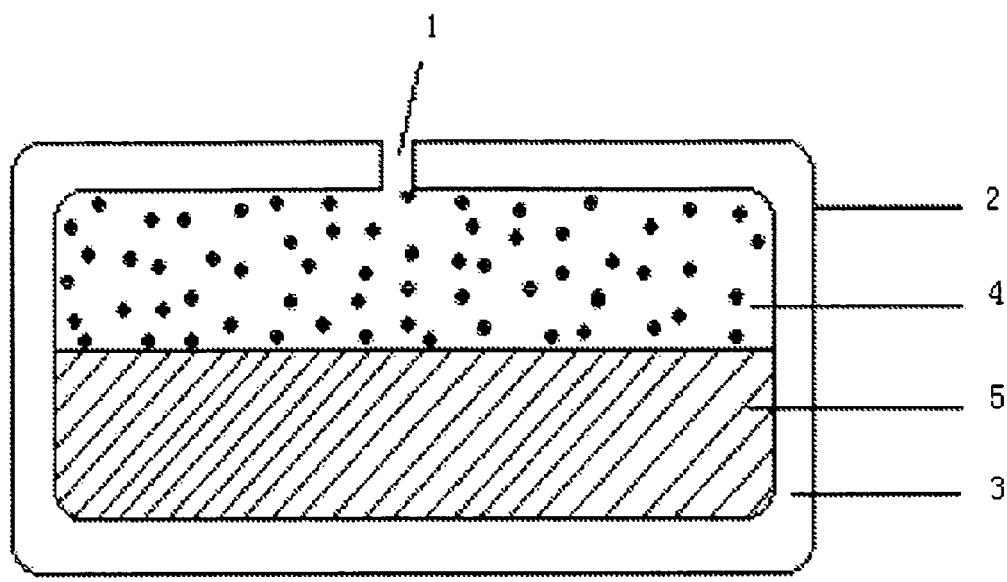
FIG. 1 is a schematic diagram showing the paliperidone double-layered osmotic pump controlled release tablet according to one embodiment of the present invention, wherein the said reference numbers are.
Figure 2:
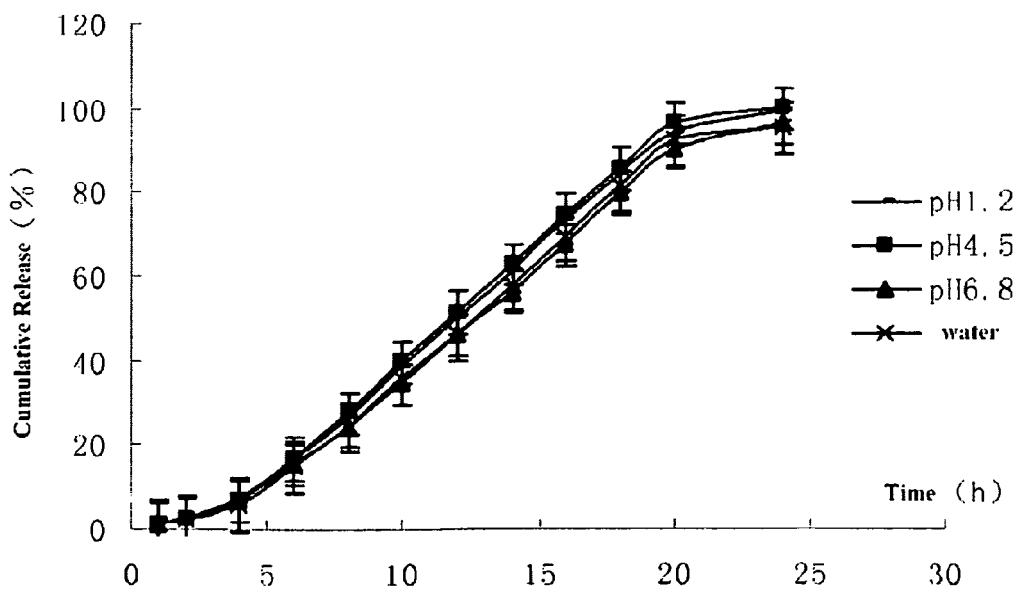
Figure 3:
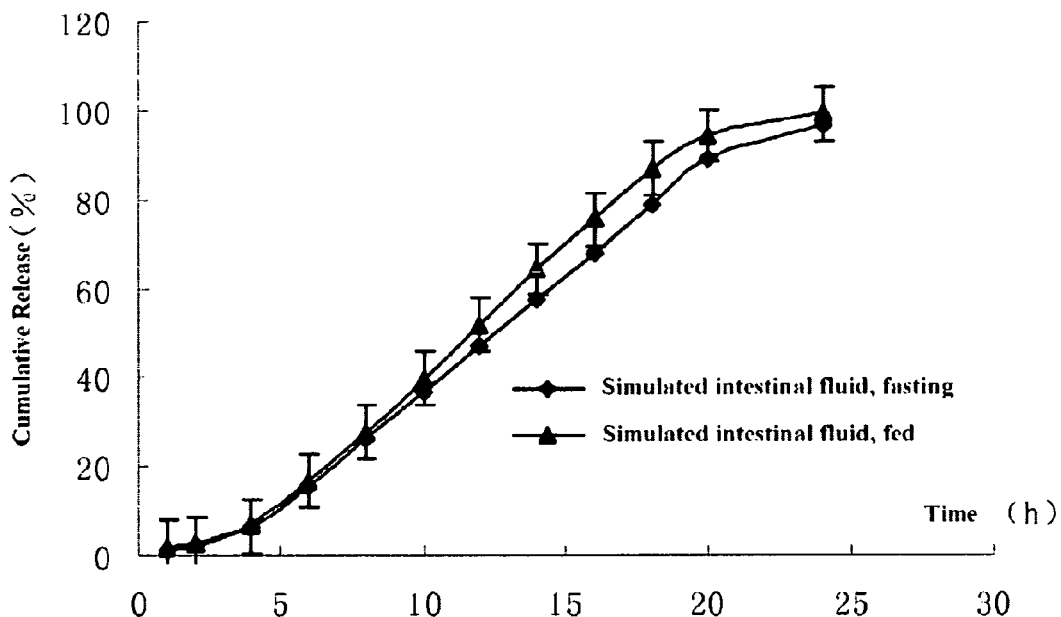
Figure 4:
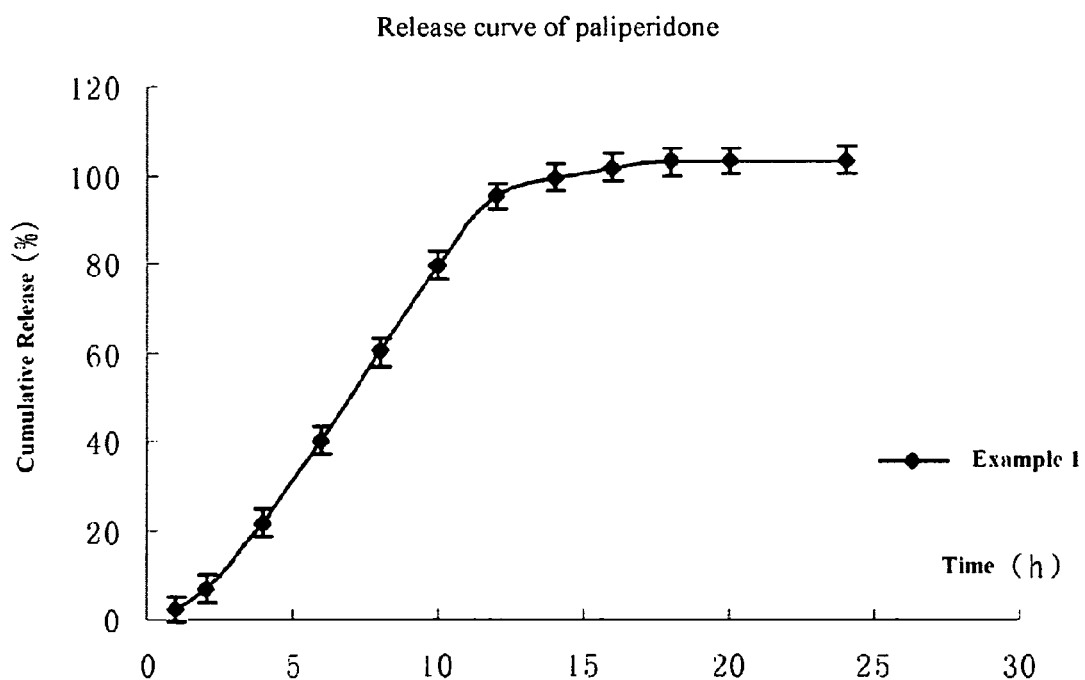
Figure 5:
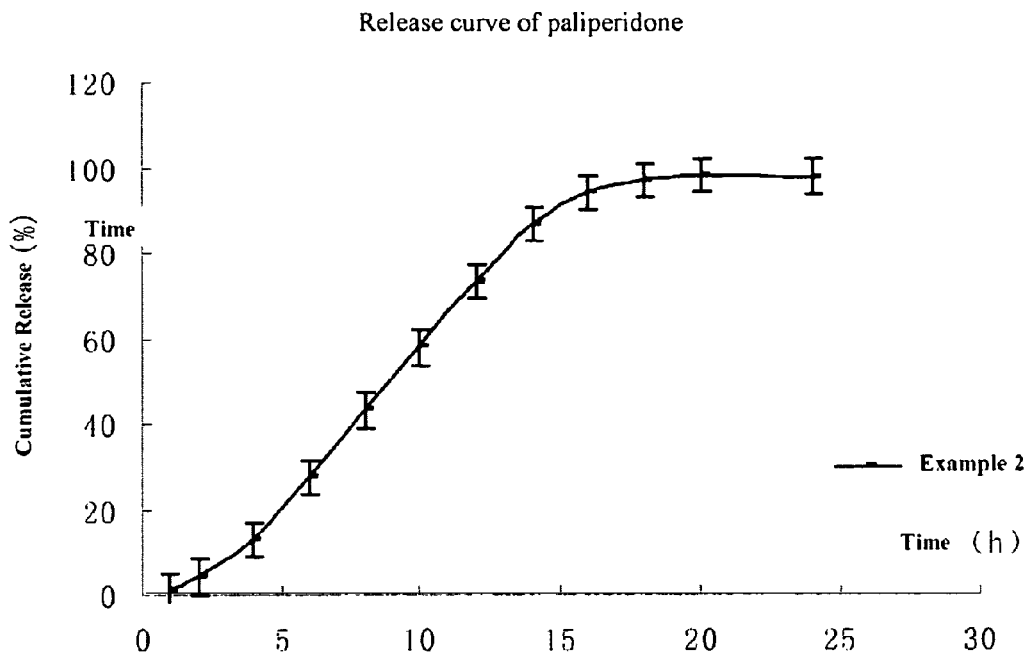
Figure 6:
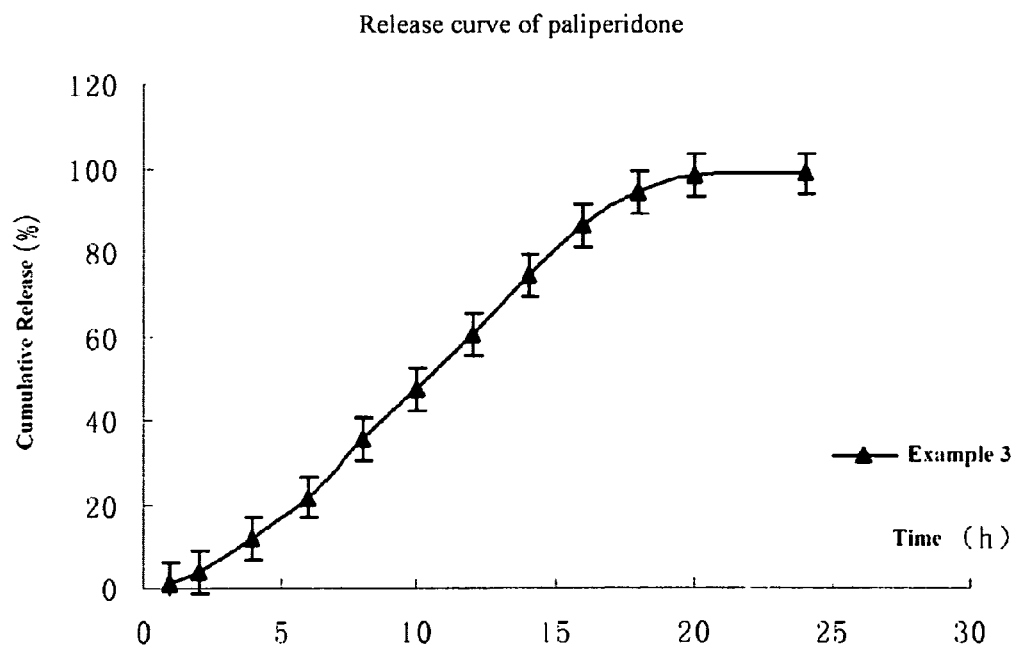
Figure 7:
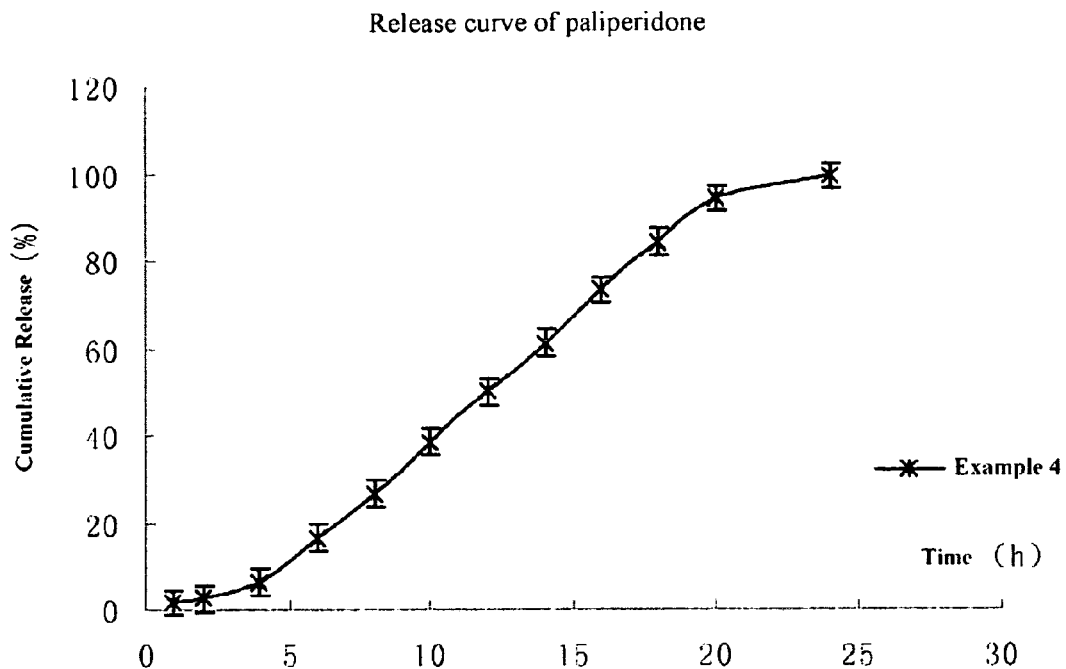
Figure 8:
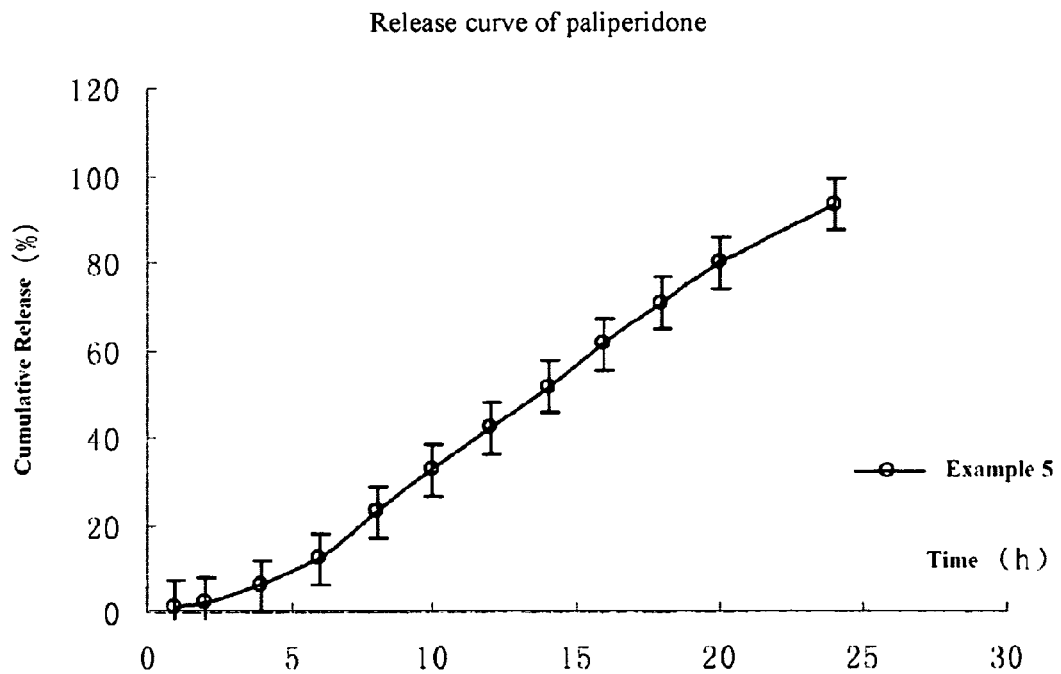
Figure 9:
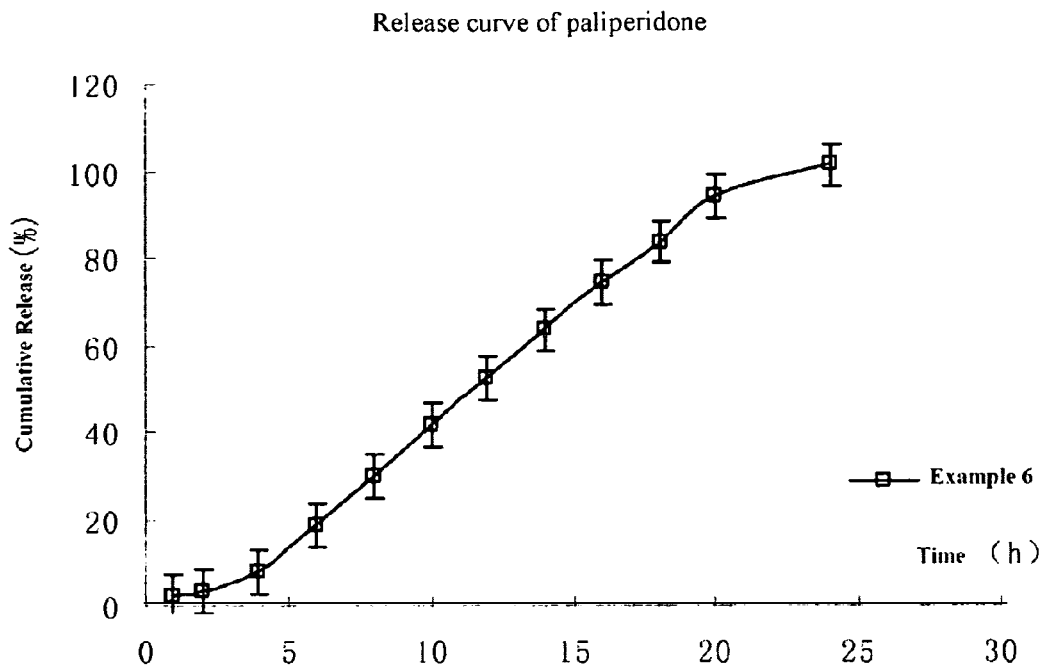
Figure 10:
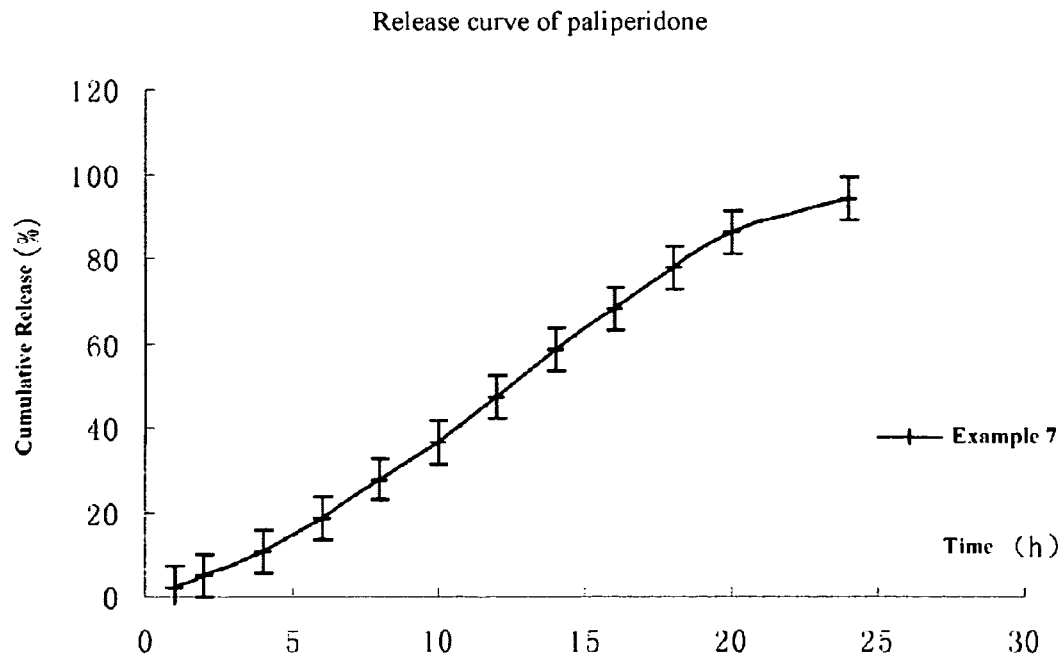
Figure 11:
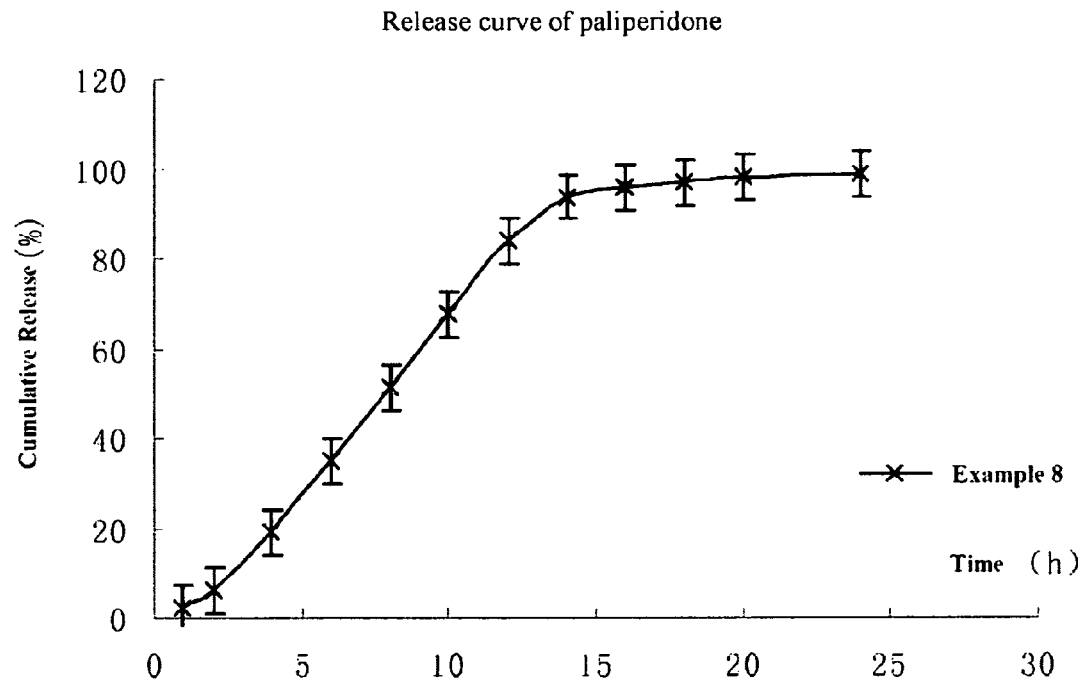
Figure 12:
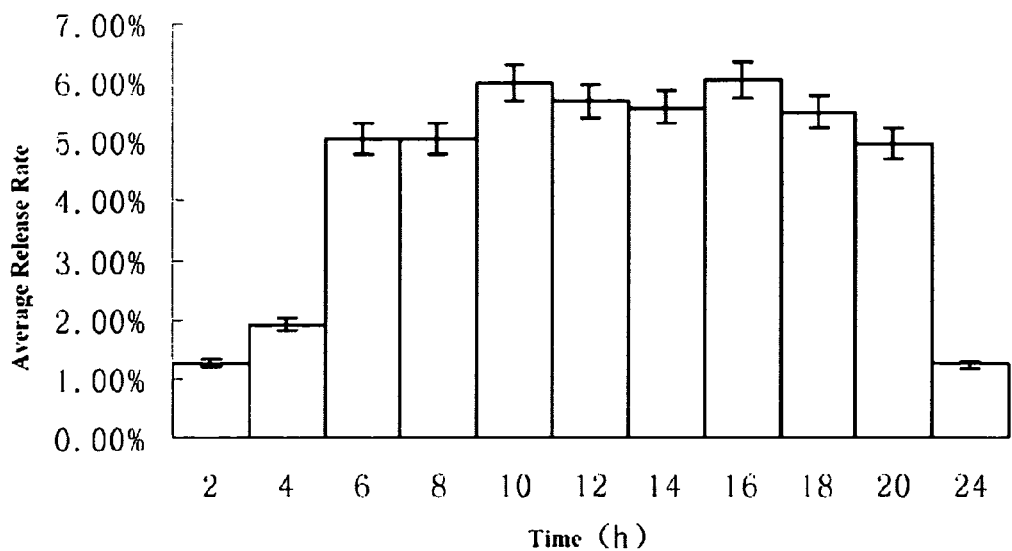
Figure 13:
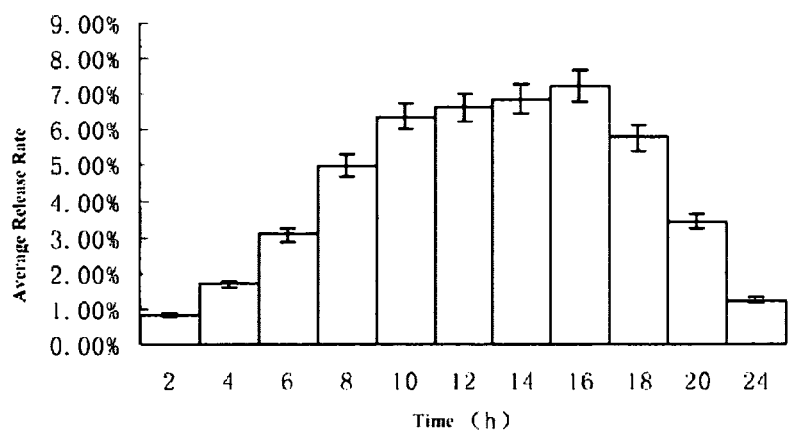

1: drug release orifice;
2: rigid membrane shell;
3: isolation layer;
4: drug layer;
5: push layer;

FIG. 2 illustrates the release curves of the paliperidone double-layered osmotic pump controlled release tablet according the present invention prepared in Example 4 in different media;

FIG. 3 illustrates the release curves of the paliperidone double-layered osmotic pump controlled release tablet according the present invention prepared in Example 4 in simulated gastrointestinal fluid;

FIG. 4 illustrates the release curve of the paliperidone double-layered osmotic pump controlled release tablet according the present invention prepared in Example 1;

FIG. 5 illustrates the release curve of the paliperidone double-layered osmotic pump controlled release tablet according the present invention prepared in Example 2;

FIG. 6 illustrates the release curve of the paliperidone double-layered osmotic pump controlled release tablet according the present invention prepared in Example 3;

FIG. 7 illustrates the release curve of the paliperidone double-layered osmotic pump controlled release tablet according the present invention prepared in Example 4;

FIG. 8 illustrates the release curve of the paliperidone double-layered osmotic pump controlled release tablet according the present invention prepared in Example 5;

FIG. 9 illustrates the release curve of the paliperidone double-layered osmotic pump controlled release tablet according the present invention prepared in Example 6;

FIG. 10 illustrates the release curve of the paliperidone double-layered osmotic pump controlled release tablet according the present invention prepared in Example 7;

FIG. 11 illustrates the release curve of the paliperidone double-layered osmotic pump controlled release tablet according the present invention prepared in Example 8;

FIG. 12 is a graph of the average release rate of the paliperidone double-layered osmotic pump controlled release tablet according the present invention prepared in Example 4;

FIG. 13 is a graph of the average release rate of the commercially available capsule-shaped paliperidone osmotic pump controlled release tablet (trade name: Invega, dosage: 6 mg) in the Comparative Example 1.

BEST MODE FOR CARRYING OUT THE INVENTION

Examples

Hereinafter, the present invention is further illustrated with the following examples. Other purposes, advantages and novel features of the present invention will be apparent for a skilled person in the art, or will be comprehended through the practice of the present invention.

The following examples record generally the exemplary dosage form and the method of preparing the osmotic pump dosage form. Unless otherwise specified, all percentages are weight percentage. The following examples are provided to facilitate the understanding of the invention, but should not be understood as a limit for the scope of the invention.

TABLE 1

The composition of Examples 1~8

| Composition | Example 1 | Example 2 | Example 3 | Example 4 | Example 5 | Example 6 | Example 7 | Example 8 |
|---|---|---|---|---|---|---|---|---|
| (1) Drug layer | | | | | | | | |
| Paliperidone (g) | 30 | 30 | 30 | 30 | 30 | 30 | 30 | 30 |
| Sodium chloride (g) | / | / | 150 | / | / | / | / | / |
| Povidone K90 (g) | 250 | 250 | / | 150 | 310 | 150 | 230 | 230 |
| copolymerized povidone S630 (g) | 300 | 400 | 500 | 310 | 150 | 310 | 230 | 230 |
| Iron oxide yellow (g) | 2.5 | 2.5 | 2.5 | 2.5 | 2.5 | 2.5 | 2.5 | 2.5 |
| silicon dioxide (g) | 7.5 | 7.5 | 2.5 | 2.5 | 2.5 | 2.5 | 2.5 | 2.5 |
| Stearic acid (g) | 5 | 5 | 5 | 5 | 5 | 5 | 5 | 5 |
| (2) Push layer | | | | | | | | |
| Sodium carboxymethyl starch (g) | 150 | 150 | 150 | 150 | 150 | 150 | 165 | 165 |
| Hypromellose (g) | 65 | 50 | 65 | 75 | 65 | 75 | 50 | 50 |
| Sodium chloride (g) | 115 | 130 | 115 | 125 | 115 | 115 | 150 | 125 |
| Carbomer (g) | / | / | 10 | 15 | 25 | 25 | / | 25 |
| Povidone K30 (g) | / | / | / | | 85 | | | |
| copolymerized povidone S630 (g) | 110 | 110 | 100 | 75 | / | 75 | 75 | 75 |
| Iron oxide red (g) | 5 | 5 | 5 | 5 | 5 | 5 | 5 | 5 |
| Stearic acid (g) | 5 | 5 | 5 | 5 | 5 | 5 | 5 | 5 |
| (3) Isolation layer | | | | | | | | |
| Paliperidone (g) | / | / | / | / | / | 1.5 | 1.0 | 0.5 |
| Hypromellose E5 (g) | 336 | 168 | 235.2 | 336 | 336 | 336 | 318 | 318 |
| Polyethylene glycol 4000 (g) | 18 | 9 | 26.6 | 18 | 18 | 18 | 36 | 36 |
| 95% Ethanol (ml) | 6000 | 3000 | 4200 | 6000 | 6000 | 6000 | 6000 | 6000 |
| Water (ml) | 1000 | 500 | 700 | 1000 | 1000 | 1000 | 1000 | 1000 |
| (4) Controlled release layer | | | | | | | | |
| Cellulose acetate (g) | 180 | 144 | / | 140 | 140 | 140 | 140 | 140 |
| Ethyl cellulose (g) | / | / | 120 | / | / | / | / | / |
| Polyethylene glycol (g) | / | / | 40 | / | / | / | / | / |
| copolymerized povidone S630 (g) | 30 | 24 | / | / | / | 7 | 10 | 10 |
| Castor oil (g) | / | / | 14.4 | / | 10 | / | / | / |
| Diethyl phthalate (g) | / | / | / | 7g | / | / | / | / |
| Acetone (ml) | 6000 | 4800 | / | 3500 | 3500 | 3500 | 3500 | 3500 |
| 95% Ethanol (ml) | 1000 | 800 | 4000 | / | / | / | / | / |
| (5) Aesthetic coating layer | | | | | | | | |
| Opadry (g) | 80 | 100 | 120 | 80 | 60 | 80 | 100 | / |
| Water (ml) | 450 | 450 | 450 | 450 | 450 | 450 | 450 | / |

Example 1

The method of preparing the paliperidone double-layered osmotic pump controlled release tablet is as follows:

The preparation of the drug layer: the drug layer composition except for stearic acid were weighted according to the formulation of Table 1 and then added into a fluidized bed after mixed uniformly, 95% ethanol was sprayed onto granules till the particle size is appropriate. After fully dried, the granules were passed through a 20-mesh sieve, and then stearic acid was added therein, and mixed to be ready for use.

The preparation of the push layer: the push layer composition except for stearic acid were weighted according to the formulation of Table 1 and then added into a fluidized bed after mixed uniformly, 95% ethanol was sprayed onto the granules till the particle size is appropriate. After fully dried, the granules were passed through a 20-mesh sieve, and then stearic acid was added therein, and mixed to be ready for use.

Press of the double-layered tablet core: the above prepared granules of drug layer and push layer was pressed into double-layered tablet core with proper hardness according to the formulation using a double-layered tablet press machine. Firstly, 119 mg granules of the drug layer composition were added into a tablet slot to perform pre-pressing, and then about 90 mg granules of the push layer composition was added so as to be pressed into the double-layered tablet core.

Coating of the isolation layer: a coating solution of the isolation layer was prepared according to the above-mentioned formulation of Table 1. The above qualified double-layered tablet cores were put into a high effective coating pan and then coated with the coating solution of the isolation layer. The coated tablets were dried for 12 hours at 45° C. to remove the residual organic solvent and water.

Coating of the controlled release layer: a coating solution of the controlled release layer was prepared according to the above-mentioned formulation of Table 1. The above double-layered tablet core with the isolation layer were coated with the coating solution of the controlled release layer. The coated tablets were dried for 12 hours at 45° C. to remove the residual organic solvent and water.

The perforation of the coated tablet: a drug release orifice with a diameter of 0.9 mm was made above the drug layer of the prepared tablet by laser drilling so that the drug layer is connected with outside.

Coating of the aesthetic coating layer: Opadry coating powder was dissolved in water to prepare the coating solution for aesthetic coating. Then the perforated controlled release tablet was coated with the coating solution. The coated tablets were dried for 12 hours at 45° C. to obtain the final product.

Example 2

Paliperidone double-layered osmotic pump controlled release tablet was prepared according to the formulation of Table 1 in the manner described in Example 1, except that 139 mg granules of the drug layer composition were used during the pressing of the double-layered tablet core.

Example 3

Paliperidone double-layered osmotic pump controlled release tablet was prepared according to the formulation of Table 1 in the manner described in Example 1, except that 138 mg granules of the drug layer composition were used during the pressing of the double-layered tablet core.

Examples 4~7

Paliperidone double-layered osmotic pump controlled release tablet was prepared according to the formulation of Table 1 in the manner described in Example 1, except that 100 mg granules of the drug layer composition were used during the pressing of the double-layered tablet core.

Example 8

Paliperidone double-layered osmotic pump controlled release tablet was prepared according to the formulation of Table 1 in the manner described in Example 4, except that the step of coating the aesthetic coating layer was not performed.

EXPERIMENTAL EXAMPLE

Release Determination

According to the method of Release Test (method I of Appendix XD, Part II, Chinese Pharmacopeia 2005), a device for Dissolution Test (method II of Appendix XD, Part II, Chinese Pharmacopeia 2005) was used to measure the drug release characteristics of the paliperidone double-layered osmotic pump controlled release tablet prepared according to the present invention, the specific steps are as follows.

(1) The paliperidone double-layered osmotic pump controlled release tablet according to the present invention was put into a small metal basket, followed by addition of 500 ml of a media (a solution of hydrochloric acid with 0.2% sodium chloride), and the rotating speed was 75 rpm. In accordance with the above method, 5 ml of solution was sampled every 2 hours in 24 hours and then centrifuged (8000 rpm, 15 min); meanwhile the media with the same temperature and volume was supplemented. The supernatant fluid was collected as the test solution.

(2) 12 mg paliperidone as control was weighted and added into a volumetric flask of 100 ml, followed by addition of methanol for dissolving and setting volume, and then the resulted solution was shaken up to obtain a uniform mixture. 5 ml of the solution was taken accurately, added into a volumetric flask of 100 ml, followed by addition of a solution of 0.2% sodium chloride in hydrochloric acid for setting volume, and then the resulted solution after being shaken up was used as the control solution.

(3) The drug release at each time point was measured through a high performance liquid chromatography by isocratic elution with an octadecyl silane-bonded silica gel as the filler and methanol-ammonium formate buffer solution (35:65) as the mobile phase under a detection wavelength of 279 nm. 20 µl of each of the above-mentioned control and the test solutions was taken accurately and then injected into the liquid chromatograph. Next, peak area was recorded, and cumulative release amounts of each tablet at different times were calculated by using the peak area in accordance with the external reference method.

Experimental Example 1

Release Rate in Different Media

Release rate was determined in four media simulating the gastrointestinal tract circumstance at different pH values, i.e., water, pH6.8, pH4.5 and pH1.2, so as to evaluate the influence of media on the release characteristics of the paliperidone double-layered osmotic pump controlled release tablet according to the present invention prepared in Example 4. The results were showed in FIG. 2.

Meanwhile, simulated intestinal fluid having the formulations showing in the following Table 2 were used to further investigate the food effect on the release characteristics of the paliperidone double-layered osmotic pump controlled release tablet according to the present invention prepared in Example 4, i.e., the release characteristics under the state of fasting and fed. The results were showed in FIG. 3.

TABLE 2

The formulations of simulated intestinal fluid

| Composition | Simulated intestinal fluid (fasting, pH6.8) | Simulated intestinal fluid (fed, pH5.0) |
|---|---|---|
| Potassium dihydrogen phosphate | 3.94 g | 8.65 g |
| Sodium hydroxide | q.s. | q.s. |
| Sodium taurocholate | 5 mM | 15 mM |
| Lecithin | 1.5 mM | 3.75 mM |
| Potassium chloride | 16.4 g | 15.2 g |
| Water | 1000 ml | 1000 ml |

As can be seen from FIG. 2, the paliperidone double-layered osmotic pump controlled release tablet according to the present invention released drugs at a predetermined rate in the four different media at different pH values, that is to say, the media has little effect on the release characteristics.

As can be seen from FIG. 3, the drug release does not have significant difference between fasting and fed in the simulated intestinal fluid. The results of the pharmacokinetic study of the paliperidone double-layered osmotic pump controlled release tablet according to the present invention in Beagle dogs coincide with the results of the release curve in vitro. Therefore, it can be foreseen that the paliperidone double-layered osmotic pump controlled release tablet could release drug uniformly when used in clinic, so as to provide more smooth and persistent therapeutic efficacy for patients.

Experimental Example 2~9 and Comparative Example 1

A solution of 0.2% sodium chloride in hydrochloric acid (29.7 ml of concentrated hydrochloric acid was diluted with water to 4000 ml) was used as the media to determine the release characteristics of the paliperidone double-layered osmotic pump controlled release tablets prepared in Examples 1~8 according to the present invention and the commercially available capsule-shaped paliperidone osmotic pump controlled release tablet (trade name: Invega, dosage: 6 mg) respectively. The results are showed in FIGS. 4~13 respectively.

FIGS. 4~11 illustrated the release curves of the paliperidone double-layered osmotic pump controlled release tablets according to the present invention prepared in Examples 1~8 respectively. As can be seen in FIGS. 4~11, the paliperidone double-layered osmotic pump controlled release tablets according to the present invention can realize the regulation of drug release rate in a certain range, and each of the said controlled release tablets (Examples 1~8) shows a gradually increasing the drug release rate at the early stage, and after a certain time, releases the drug constantly at a predetermined rate, so as to achieve the predetermined drug release mode of "increasing first and then being constant". Thus it will ensure that the paliperidone double-layered osmotic pump controlled release tablet of the present invention can achieve rapidly a blood concentration that is effective for treatment at the early stage of drug release, and then release drug at a steady and constant speed at the later stage of drug release, thereby maintaining a more smooth curve of blood concentration, decreasing the fluctuation of blood concentration, reducing the adverse reactions (mainly extrapyramidal symptoms) of nervous system of atypical antischizophrenic drugs, and improving the safety, efficacy and compliance of administration significantly.

FIGS. 12~13 show the average release rates of the paliperidone double-layered osmotic pump controlled release tablet prepared in Example 4 according the present invention and the commercially available capsule-shaped paliperidone osmotic pump controlled release tablet respectively. It can be seen from the comparison of FIG. 12 and FIG. 13 that the paliperidone double-layered osmotic pump controlled release tablet according the present invention has a more steady average release rate compared with the commercially available capsule-shaped paliperidone osmotic pump controlled release tablet, and thereby it is better for decreasing the fluctuation of blood concentration and reducing the occurrence of the adverse reactions of the drug.

INDUSTRIAL APPLICABILITY

The present invention adopts the double-layered osmotic pump controlled release system such that not only the production process steps is simplified, the workload during preparing process is reduced, and the production cycle period is shortened, but also the production equipments used is common without requirement of any special equipment, the operation is simple, thereby decreasing the investment cost at the initial stage of production process and being suitable for industrial production.

In addition, the selected novel excipient for the tablet core have good thermal stability, high glass transition temperature and good oral safety, so as to solve the problem resulting from using polyoxyethylene as the main excipient of the tablet core. The formulation provided by the present invention has good compressibility and is suitable for high speed tablet-pressing, and the pressed tablet core has a smooth surface with good hardness. Furthermore, the excipient of the present dosage form has a lower cost, and thus can reduce the production cost significantly. In addition, the process for the present dosage form is mature and steady, and has a broader industrial prospect for industrial production.

What is claimed is:

1. A paliperidone double layered osmotic pump controlled release tablet comprising, based on the total weight of the controlled release tablet,
   0.1 to 15% of a moisture-permeable rigid membrane shell having one or more drug release orifices at one end thereof, which is made of the controlled release layer composition comprising a semi-permeable polymer, a porogen and/or a plasticizer;
   15 to 60% of a push layer inside the rigid membrane shell and away from the side of the drug release orifice, which is made of a push layer composition comprising, based on the total weight of the push layer composition, 20 to 80% of an expansion material, 10 to 45% of an osmotic agent, 0 to 30% of a binder, and optionally, a colorant and a lubricant;
   10 to 80% of a drug layer inside the rigid membrane shell, adjacent to the release orifices and directly contacting with the push layer, which is made of a drug layer composition comprising, based on the total weight of the drug layer composition, 0.1 to 25% of a pharmaceutically active ingredient, 65 to 99% of one or more hydrophilic polymer carriers, and optionally, an osmotic agent, a colorant, a lubricant and an antistatic agent;
   0.1 to 30% of an isolation layer located between the inside surfaces of the rigid membrane shell and the tablet core consisting of the drug layer and the push layer, which is made of an isolation layer composition comprising 0 to 30% of a pharmaceutically active ingredient based on the total weight of the isolation layer composition, and one or more hydrophilic polymers;
   0 to 20% of an optional aesthetic coating layer coated on the outer surface of the rigid membrane shell, which is made of an aesthetic coating layer composition comprising coating powder for forming the aesthetic coating, and optionally, one or more excipients selected from the group consisting of colorant, a plasticizer, an opacifying agent, and an anti-sticking agent;
   wherein the hydrophilic polymer carrier in the drug layer is selected from the group consisting of povidone, copolymerized povidone, carbomer, hydroxypropyl cellulose, hypromellose and mixtures thereof;
   wherein the said paliperidone double layered osmotic pump controlled release tablet shows an gradually increasing release rate at early stage and maintains a constant release rate at later stage, wherein said pharmaceutically active ingredient is selected from the group consisting of paliperidone and pharmaceutically acceptable salts and esters thereof.

2. The paliperidone double layered osmotic pump controlled release tablet according to claim 1, wherein the proportion of the hydrophilic polymer carriers in the drug layer composition is 70 to 95% based on total weight of the drug layer composition.

3. The paliperidone double layered osmotic pump controlled release tablet according to claim 1, wherein the duration of the early stage with the gradually increasing release rate is at least 3 hours, and the duration of the later stage maintaining the constant release rate is at least 5 hours.

4. The paliperidone double layered osmotic pump controlled release tablet according to claim 1, wherein, based on the total weight of controlled release tablet, the weight percentages of various layers are as follows: the drug layer takes up 20 to 70 wt %; the push layer takes up 20 to 55 wt %; the isolation layer takes up 2 to 30 wt %; the membrane shell takes up 0.5 to 12 wt %; and the aesthetic coating layer takes up 0.1 to 15 wt %.

5. The paliperidone double layered osmotic pump controlled release tablet according to claim 1, wherein the pharmaceutically active ingredient takes up 1 to 20 wt % in the drug layer composition, based on the total weight of the drug layer.

6. The paliperidone double layered osmotic pump controlled release tablet according to claim 1, wherein the pharmaceutically active ingredient takes up 0.1 to 15 wt % in the isolation layer composition based on the total weight of the isolation layer composition.

7. The paliperidone double layered osmotic pump controlled release tablet according to claim 1, wherein the antistatic agent in the drug layer is selected from the group consisting of silicon dioxide, stearic acid, polyethylene glycol and mixtures thereof.

8. The paliperidone double layered osmotic pump controlled release tablet according to claim 1, wherein, based on the total weight of the drug layer, the antistatic agent takes up 0 to 8 wt % in the drug layer.

9. The paliperidone double layered osmotic pump controlled release tablet according to claim 1, wherein the osmotic agent is selected from the group consisting of sodium chloride, lactose, mannitol, sorbitol, glucose, sucrose, fructose and mixtures thereof.

10. The paliperidone double layered osmotic pump controlled release tablet according to claim 1, wherein the semipermeable polymer in the controlled release layer composition is selected from the group consisting of cellulose acetate, ethyl cellulose, acrylic resin and mixtures thereof.

11. The paliperidone double layered osmotic pump controlled release tablet according to claim 1, wherein the porogen in the controlled release layer composition is selected from the group consisting of glycerin, povidone, copolymerized povidone, propylene glycol, polyethylene glycol, water-soluble inorganic salts and mixtures thereof.

12. The paliperidone double layered osmotic pump controlled release tablet according to claim 1, wherein the plasticizer in the controlled release layer composition is selected from the group consisting of dimethyl phthalate, diethyl phthalate, dibutyl sebacate, triethyl citrate, tributyl citrate, tributyl acetylcitrate, glycerol acetate, castor oil and mixtures thereof.

13. The paliperidone double layered osmotic pump controlled release tablet according to claim 1, wherein the expansion material in the push layer is selected from the group consisting of sodium carboxymethyl starch, low substituted hypromellose, hypromellose, hydroxypropyl cellulose, croscarmellose sodium, crospovidone, carbomer and mixtures thereof.

14. The paliperidone double layered osmotic pump controlled release tablet according to claim 1, wherein the binder in the push layer is selected from the group consisting of povidone, copolymerized povidone, hypromellose and mixtures thereof.

15. The paliperidone double layered osmotic pump controlled release tablet according to claim 1, wherein the hydrophilic polymer in the isolation layer is selected from the group consisting of hypromellose, povidone, copolymerized povidone, hydroxyethyl cellulose, polyoxyethylene, polyethylene glycol and mixtures thereof.

16. A method for preparing the paliperidone double layered osmotic pump controlled release tablet according to claim 1, comprising the steps of:
(1) uniformly mixing the components of the drug layer composition in formulated amounts, and then preparing granules of the drug layer composition;
(2) uniformly mixing the components of the push layer composition in formulated amounts, and then preparing granules of the push layer composition;
(3) pressing the above prepared granules of the drug layer composition and the push layer composition formulated amounts into double-layered tablet core;
(4) coating the above double-layered tablet core with the isolation layer composition;
(5) coating the double-layered tablet core coated with the isolation layer composition with the controlled release layer composition;
(6) perforating a drug-release orifice on the coated tablet obtained in step (5);
(7) optionally, coating the controlled release tablet obtained in step (6) with the aesthetic coating layer composition.

17. The paliperidone double layered osmotic pump controlled release tablet according to claim 1, wherein the duration of the early stage with the gradually increasing release rate is 5 hours.

18. The paliperidone double layered osmotic pump controlled release tablet according to claim 1, wherein the duration of the later stage maintaining the constant release rate is 6 to 12 hours.

19. The paliperidone double layered osmotic pump controlled release tablet according to claim 1, wherein the osmotic agent is sodium chloride or lactose.

20. The paliperidone double layered osmotic pump controlled release tablet according to claim 1, wherein the antistatic agent in the drug layer is silicon dioxide.

21. The paliperidone double layered osmotic pump controlled release tablet according to claim 1, wherein the expansion material in the push layer is a mixture of sodium carboxymethyl starch, carbomer and hypromellose.

22. The paliperidone double layered osmotic pump controlled release tablet according to claim 1, wherein the hydrophilic polymer in the isolation layer is selected from the group consisting of hypromellose, povidone, copolymerized povidone, polyethylene glycol and mixtures thereof.

* * * * *